(12) United States Patent
Maran et al.

(10) Patent No.: US 6,730,665 B1
(45) Date of Patent: May 4, 2004

(54) TREATMENT OF BONE CANCER

(75) Inventors: Avudaiappan Maran, Rochester, MN (US); Russell T. Turner, Wabasha, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/018,287

(22) PCT Filed: May 12, 2000

(86) PCT No.: PCT/US00/13101

§ 371 (c)(1),
(2), (4) Date: Apr. 23, 2002

(87) PCT Pub. No.: WO00/67757

PCT Pub. Date: Nov. 16, 2000

Related U.S. Application Data

(60) Provisional application No. 60/133,740, filed on May 12, 1999.

(51) Int. Cl.[7] ............................................. A61K 31/56
(52) U.S. Cl. ....................................................... 514/182
(58) Field of Search ......................................... 514/182

(56) References Cited

U.S. PATENT DOCUMENTS

| 5,643,900 A | * | 7/1997 | Fotsis et al. | |
| 5,958,892 A | | 9/1999 | Mukhopadhyay et al. | .... 514/44 |

FOREIGN PATENT DOCUMENTS

| WO | WO 98/04291 | 2/1998 |

OTHER PUBLICATIONS

Dorlands's Illustrated Medical Dictionary, 28th Edition, p. 1485, 1994.*

Borke et al., "Epitopes of the Human Erythrocyte $Ca^{2+}$-$Mg^{2+}$ ATPase Pump in Human Osteoblast-Like Cell Plasma Membranes," *J. Clin. Endocrin. Metab.*, 1988, 67(6):1299-1304.

Fajardo et al., "A comparative study of the effects of genistein and 2-methoxyestradiol on the proteolytic balance and tumour cell proliferation," *Br. J. Cancer*, 1999, 80(1/2):17-24.

He and Cushman, "A Versatile Synthesis of 2-Methoxyestradiol, an Endogenous Metabolite of Estradiol Which Inhibits Tubulin Polymerization by Binding to the Colchicine Binding Site," *Bioorganic & Medicinal Chemistry Letters*, 1994, 4(14):1725-1728.

Himelstein, "Osteosarcoma and other bone cancers," *Curr. Opin. Oncol.*, 1996, 10:326-333.

Lynch et al., "Apoptosis During Bone-Like Tissue Development In Vitro," *J. Cell. Biochem.*, 1998, 68:31-49.

Merriam et al., "Comparative Properties of the Catechol Estrogens, I: Methylation by Catechol-O-Methyltransferase and Binding to Cytosol Estrogen Receptors," *Steroids*, 1980, 36:1-11.

Oltvai et al., "Bcl-2 Heterodimerizes In Vivo with a Conserved Homolog, Bax, That Accelerates Programed Cell Death," *Cell*, 1993, 74:609-619.

Turner et al., "Differential Responses of Estrogen Target Tissues in Rats Including Bone to Clomiphene, Enclomiphene, and Zuclomiphene," *Endocrinology*, 1998, 139(9):3712-3720.

Wang and Cushman, "An Optimized Synthesis of 2-Methoxyestradiol, a Naturally Occurring Human Metabolite with Anticancer Activity," *Synthetic Comm.*, 1998, 28(23):4431-4437.

Fotsis et al., "The endogenous oestrogen metabolite 2-methoxyoestradiol inhibits angiogenesis and suppresses tumour growth," *Nature*, 1994, 36:237-239.

Maran et al., "2-Methoxyestradiol Induces Interferon Gene Expression and Apoptosis in Osteosarcoma Cells," *Bone*, 2002, 30:393-398.

LaVallee et al., "2-Methoxyestradiol Up-Regulates Death Receptor 5 and Induces Apoptosis through Activation of the Extrinsic Pathway," *Cancer Research*, 2003, 63:468-475.

"Soft Tissue Sarcomas: Questions and Answers, Cancer Facts 6.12", 2000, National Cancer Institute website http://cis.nci.nih.gov/fact/6_12.htm, 7 pps.

Cotran et al., *Pathologic Basis of Disease*, Sixth Edition, 1999, W.B. Saunders Company, pp. 1240-1242.

* cited by examiner

*Primary Examiner*—Dwayne C. Jones
(74) *Attorney, Agent, or Firm*—Fish & Richardson P.C., P.A.

(57) ABSTRACT

Methods for killing bone cancer cells and for treating bone cancer are described.

9 Claims, 8 Drawing Sheets

TREATMENT OF BONE CANCER

CROSS-REFERENCE TO RELATED APPLICATIONS

This application is a U.S.C. § 371 Application of PCT/US00/13101, filed May 12, 2000, which claims priority from U.S. Provisional Application Serial No. 60/133,740, filed May 12, 1999.

TECHNICAL FIELD

The invention relates to killing bone cancer cells and treating bone cancers.

BACKGROUND

Osteosarcoma is a malignant tumor of bone, which is most prevalent in adolescents and young adults. Osteosarcoma accounts for approximately 5% of the tumors in childhood and 80% of these tumors originate around the knee. The prognosis is often poor and within 1 year after commencing definitive therapy, about 30% of patients diagnosed with osteosarcoma will develop lung metastasis. The prognosis appears to be determined by the site of metastases and surgical resectability of the metastatic disease, either at diagnosis or following a variable period of chemotherapy. Patients who have complete surgical ablation of the primary and metastatic tumor (when confined to the lung) following chemotherapy may attain long-term survival, although event-free survival remains about 20% for patients with metastatic disease at diagnosis. Patients developing recurrent disease often have a poor prognosis and die within 1 year of the development of metastatic disease. Chemotherapy is often ineffective, resulting in a high mortality rate. Hence, it is important that new therapeutic approaches are evaluated for this malignant disease.

SUMMARY

The invention is based on the discovery that 2-methoxy estradiol (2ME) is cytotoxic to osteosarcoma cells in vitro and can reduce longitudinal bone growth rate and growth plate thickness in animals. Thus, the invention provides methods for treating bone cancers and methods for killing bone cancer cells, including osteosarcomas and chondrosarcomas.

In one aspect, the invention features a method for treating bone cancer in a patient. The method includes administering an amount of 2ME to the patient, wherein the amount of 2ME is cytotoxic to bone cancer cells. The bone cancer can be an osteosarcoma or a chondrosarcoma.

The invention also features a method for killing bone cancer cells. The method includes contacting the bone cancer cells with an amount of 2ME, wherein the amount of 2ME is cytotoxic to the bone cancer cells. The bone cancer cells can be human cells, osteosarcoma cells, or chondrosarcoma cells. The cells can be contacted in vitro or in vivo.

In another aspect, the invention features use of 2ME in the manufacture of a medicament for treatment of bone cancer.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
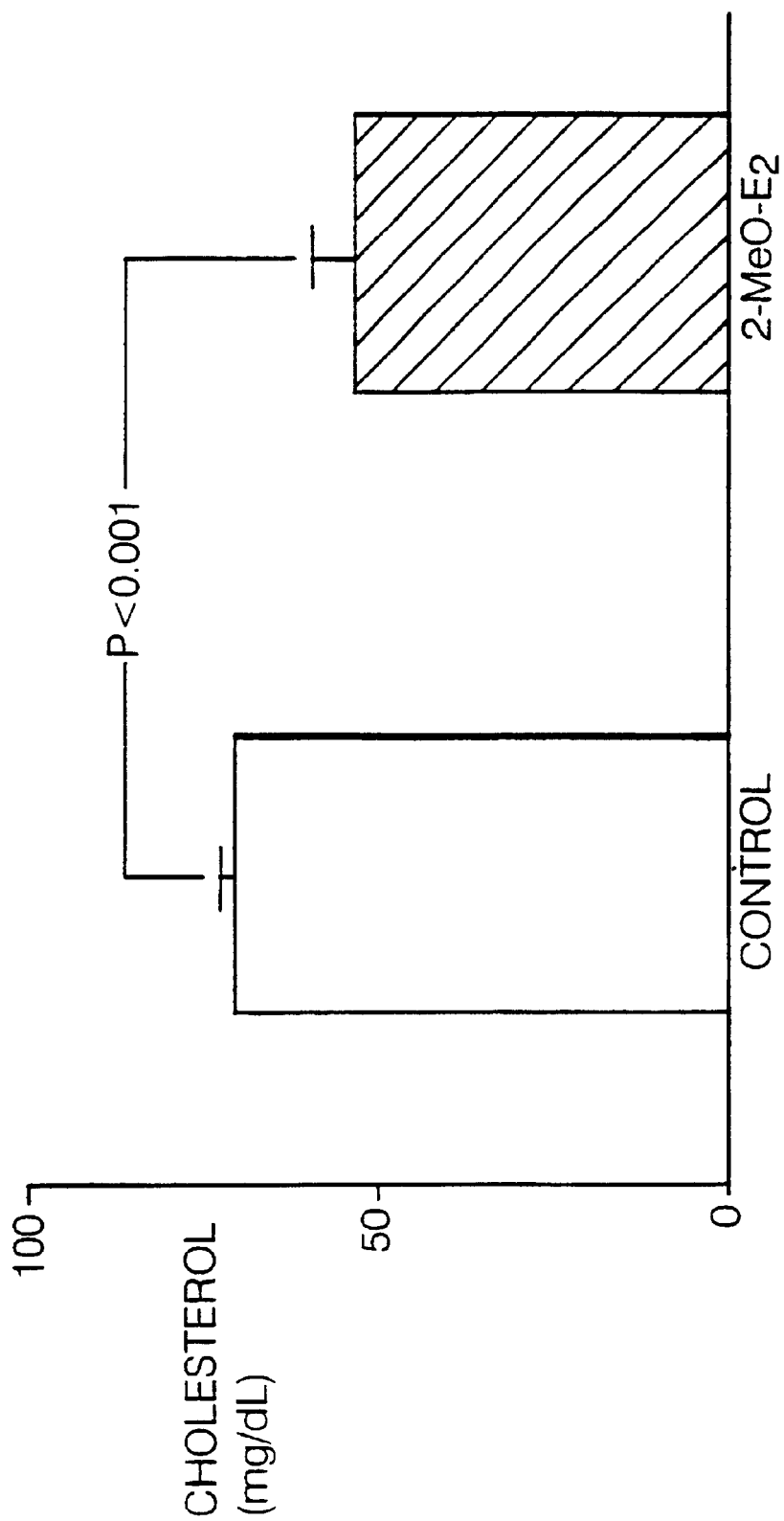
FIG. 1 is a graph depicting that 2ME treatment decreased serum cholesterol. Values are reported as mean±SE, n=8–9.

In one aspect, the invention features a method for killing bone cancer cells. Bone cancer cells include primary bone cancer cells such as osteosarcoma cells, cells from Ewing's family of tumors, chondrosarcoma cells, malignant giant cell tumor cells, malignant fibrous histiocytoma cells, and adamantinoma cells, as well as secondary bone cancer cells that have metastasized from other tissues, including breast, lung, prostate, and kidney. The method includes contacting a bone cancer cell with an amount of 2-methoxyestradiol (2ME) that is cytotoxic to the bone cancer cells. 2ME is an endogenous metabolite of 17β-estradiol (estradiol, $E_2$) that is produced in vivo primarily by hepatic hydroxylation of $E_2$ to 2-hydroxyestradiol (2OHE) followed by O-methylation at numerous peripheral sites. 2ME is available commercially, for example, from Sigmna Chemical Company (St. Louis, Mo.), or can be synthesized. See, for example, He and Cushman, *Bioorganic & Medicinal Chemistry Letters*, 1994, 4(14):1725–1728, for a description of 2ME synthesis from estradiol; and Wang and Cushman, *Synthetic Communications*, 1998, 28(23):4431–4437, for a description of 2ME synthesis from an ether of 2-formylestradiol.

As described herein, continuous treatment of osteosarcoma cells and immortalized cell lines with 2 $\mu$M 2ME reduced cell survival by 85% after 72 hours, whereas at the same concentration, 2OHE, $E_2$, and 2-methoxyestrone had minimal impact. At 20 $\mu$M concentrations, 2ME, 2OHE, and $E_2$ reduced cell survival by 95%, 60%, and 50% respectively. Treatment of human osteosarcoma cells with an antiestrogen did not affect the growth inhibition by 2ME. Thus, 2ME selectively inhibits growth of osteosarcoma cells. Growth of normal osteoblasts was not affected, further indicating the usefulness of 2ME as a treatment for bone metastases.

The concentration of 2ME cytotoxic to bone cancer cells in a mammal may vary, depending on a number of factors, including the preferred dosage of 2ME to be administered, the formulation of the compound excipients, and the route of administration. The optimal dosage of 2ME to be administered may also depend on such variables as the overall health status of the particular patient. 2ME may be formulated into pharmaceutical compositions by admixture with pharmaceutically acceptable non-toxic excipients or carriers. Such compounds and compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration may be prepared as desired using standard methods.

Formulations for parenteral administration may contain as common excipients sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration.

As described herein, treatment of rats with 2ME resulted in pronounced changes in the growth plate, including reductions in overall growth plate height and height of the hypertrophic and proliferative zones. Additionally, there was a dramatic reduction in the rate of longitudinal bone growth. These changes appeared to be specific to the growth plate, as 2ME treatment did not alter bone architecture and turnover.

Effects of 2ME on rat tibia were not identical to the effects of estradiol or selective estrogen receptor modulators (SERMs) such as raloxifene, idexifene, and tamoxifen. Estradiol and 2ME were similar in that each inhibited longitudinal bone growth, but estradiol inhibited radial bone growth and cancellous bone turnover in normal rats, while 2ME did not. 2ME had actions that were similar to the actions of SERMS in that they both reduced serum cholesterol. Estradiol treatment also lowers serum cholesterol in rats and this response is believed to be estrogen receptor-mediated. 2ME, however, has negligible affinity for estrogen receptors. Therefore, the mechanism for the hypocholesterolemic effect of 2ME is unknown. It is not likely to be similar to the pathway for 17$\beta$-estradiol.

2ME differs from SERMs in that the estrogen metabolite did not decrease uterine weight, whereas SERMs typically decrease uterine weight. 2ME also differs from the steroidal antiestrogens (e.g. ICI 182,780), which increase bone turnover and induce hypercholesterolemia in normal female rats. Because it does not have an effect on the classical estrogen target tissues, it is unlikely that the effects of 2ME on the growth plate are estrogen-receptor mediated.

The observed decrease in the longitudinal growth rate in 2ME treated rats indicates that this estrogen metabolite inhibits endochondral ossification. The decrease in height of the proliferative zone indicates that the decreased growth rate is due at least in part, to decreased cartilage cell proliferation. Although vascular invasion of the calcified hypertrophic zone of the growth plate was greatly reduced in rate, based on the results obtained using the fluorochrome labeling method, there was a near complete destruction of the hypertrophic zone in the 2ME treated rats. These findings indicate that the rate of vascular invasion, although slowed, exceeds cartilage matrix synthesis. This change in cartilage metabolism would result in premature epiphyseal closure.

Estrogen is believed to play a pivotal role in mediating epiphyseal closure in men as well as in women. Functional disruption of the gene for estrogen receptor alpha results in prolongation of longitudinal bone growth and severe osteopenia, as does disruption of the aromatase gene. Results described herein indicate that 2ME has target tissue-selective skeletal activity and may contribute to normal epiphyseal closure by inhibiting proliferation of growth plate cartilage cells. Additionally, if the actions of 2ME on growth plate are non-estrogen receptor mediated, then 2ME may be useful for treatment of rare abnormalities of the skeleton, which are due to target cell resistance to estrogen resulting from abnormalities in the estrogen receptor. Because of the reduced potential for stimulation of reproductive tissues, 2ME may also be of interest clinically to induce epiphyseal closure.

The invention will be further described in the following examples, which do not limit the scope of the invention described in the claims.

EXAMPLES

Example 1

Methods and Materials

All studies were approved by the Institutional Animal Care and Use Committee of the Mayo Clinic, Rochester, Minn. Rats were kept in plastic cages (3 per cage) under standard conditions of a 12 hr dark and 12 hr light cycle with food (Purina Laboratory rodent diet 5001, Ralston-Purina, St. Louis, Mo.) and water ad libitum. Rooms were maintained at a temperature of 24° C.

Twenty-five female 3-month-old Fisher 344 rats, weighing approximately 141–160 g, were purchased from Harlan Sprague Dawley (Madison, Wis.). The rats were divided into 3 groups (8 or 9 rats/group) of a baseline group that was sacrificed on the first day of treatment, a control group that was treated with carrier (liposomes) only, and a 2ME treatment group. Rats in the treatment group were given orally, by gavage, a therapeutic dosage of 2ME (100 mg/kg/day) for 13 days. Fluorochromes were given juxta tail vein. Declomycin (20 mg/kg) was given on the first day of treatment and calcein (15 mg/kg) two days prior to sacrifice, in order to label mineralizing bone and cartilage. Twenty-four hours after the last dosage, rats were anesthetized with ketamine HCl (100 mg/kg):xylaxine HCl (10 mg/kg) and sacrificed by decapitation. Trunk blood was collected and serum frozen at −70° C. prior to measurement of serum cholesterol. Tibiae were quickly excised and fixed for histomorphometry in a solution of 70% ethanol.

Bone histomorphometry Histomorphometric measurements were performed with the OsteoMeasure Analysis System (OsteoMetrics, Atlanta, Ga.), which consisted of a Pentium 1133 computer coupled to a photomicroscope and image analysis system. The image system consisted of a high resolution color video camera (Sony DXC-970 MD) that records the image specimen through the microscope (Olympus BH-2, New Hyde Park, N.Y.) and displays the image on a view sonic video monitor that registers the movement of a digitizing pen on a graphics table (OsteoTablet, OsteoMetrics, Atlanta, Ga.). The region of interest was traced, and the line lengths and area bounded by lines were calculated automatically.

Cortical bone measurements Ground transverse sections, cut at a site just proximal to the tibia-fibula synostosis, were prepared for histomorphometric analysis of cortical bone as described by Merriam, G. R. et al., *Steroids*, 1980, 136: 1–11. The following values were obtained as described by Turner, R. T. et al., *Endocrinology*, 1998, 139:3712–3720: 1) cross-sectional bone area; 2) medullary area: 3) cortical bone area: 4) periosteal perimeter; 5) endocortical perimeter; 6) periosteal bone formation rate, calculated as the area of bone between the declomycin label given at the start of the experiment and periosteal perimeter divided by the post-labeling period of 11 days; 7) periosteal mineral apposition rate, an index of osteoblast activity which is calculated as the periosteal bone formation rate divided by the label perimeter; and 8) periosteal label perimeter, an index of osteoblast number, defined as the periosteal perimeter labeled with calcein.

Cancellous bone measurements on stained sections The proximal tibial metaphysis was dehydrated in a series of increasing concentrations of ethanol, embedded without demineralization in a mixture of methyimethacrylate-2-hydroxyethyl and methacrylate (12.5:1) to retain the fluorochrome labels, and sectioned at a thickness of 5 $\mu$m (Reichert-Jung Model 2065 Microtome, Heidelberg Germany). Sections were stained with toluidine blue. A standard sampling site was established in the secondary spongiosa of the metaphysis, 1 mm distal to the calcein label that was deposited at the metaphyseal growth plate, its center perpendicular to the long axis of each bone and extending 2.0 mm distal to the starting point. This method adjusts for longitudinal growth such that only the portion of the secondary spongiosa present throughout the experiment was sampled. A total metaphyseal area of 2.88 mm$^2$ was sampled for each section.

Bone volume measurements Cancellous bone area and cancellous perimeter were determined as described by Turner, R. T. et al., 1998, supra. The following indices of trabecular architecture were calculated: 1) trabecular thickness; 2) trabecular number; and 3) trabecular separation.

Bone formation measurements and calculations Bone formation rate (%/day, tissue area referent) was calculated as the double-labeled perimeter ($\mu$n) multiplied by the mineral apposition rate ($\mu$m/day) and divided by the tissue area (mm$^2$); bone formation rate (perimeter referent) was calculated as the double-labeled perimeter ($\mu$m) multiplied by the mineral apposition rate ($\mu$m/day) and divided by the total bone perimeter (mm); mineral apposition rate was calculated as the mean distance between the declomycin label and the calcein label by the time interval (11 days); and double-labeled perimeter (tissue are referent) was measured as the length with declomycin and calcein labels (mm/mm$^2$ of cancellous tissue area).

Growth Plate Measurements The longitudinal bone growth rate was measured at 5 equally spaced sites across the growth plate as the distance between the declomycin and calcein labels that had been deposited into the mineralizing front of the hypertrophic zone of the growth plate divided by the 11 day interval between application of the sequential fluorochromes.

Growth plate thickness was measured as the mean distance between the zone of vascular invasion and the resting zone. Thicknesses of the proliferative zone and hypertrophic zone were also measured.

Statistical Analyses All values are expressed as mean±standard error (SE). Significant differences between groups were determined by Fisher's Protected Least Significant Difference post hoc test for multiple group comparisons following detection of significance by 1-way ANOVA. Significance was considered at p values $\leq 0.05$.

Example 2

Altered Growth Plate Histomorphometry with 2ME Treatment

Figure 2:
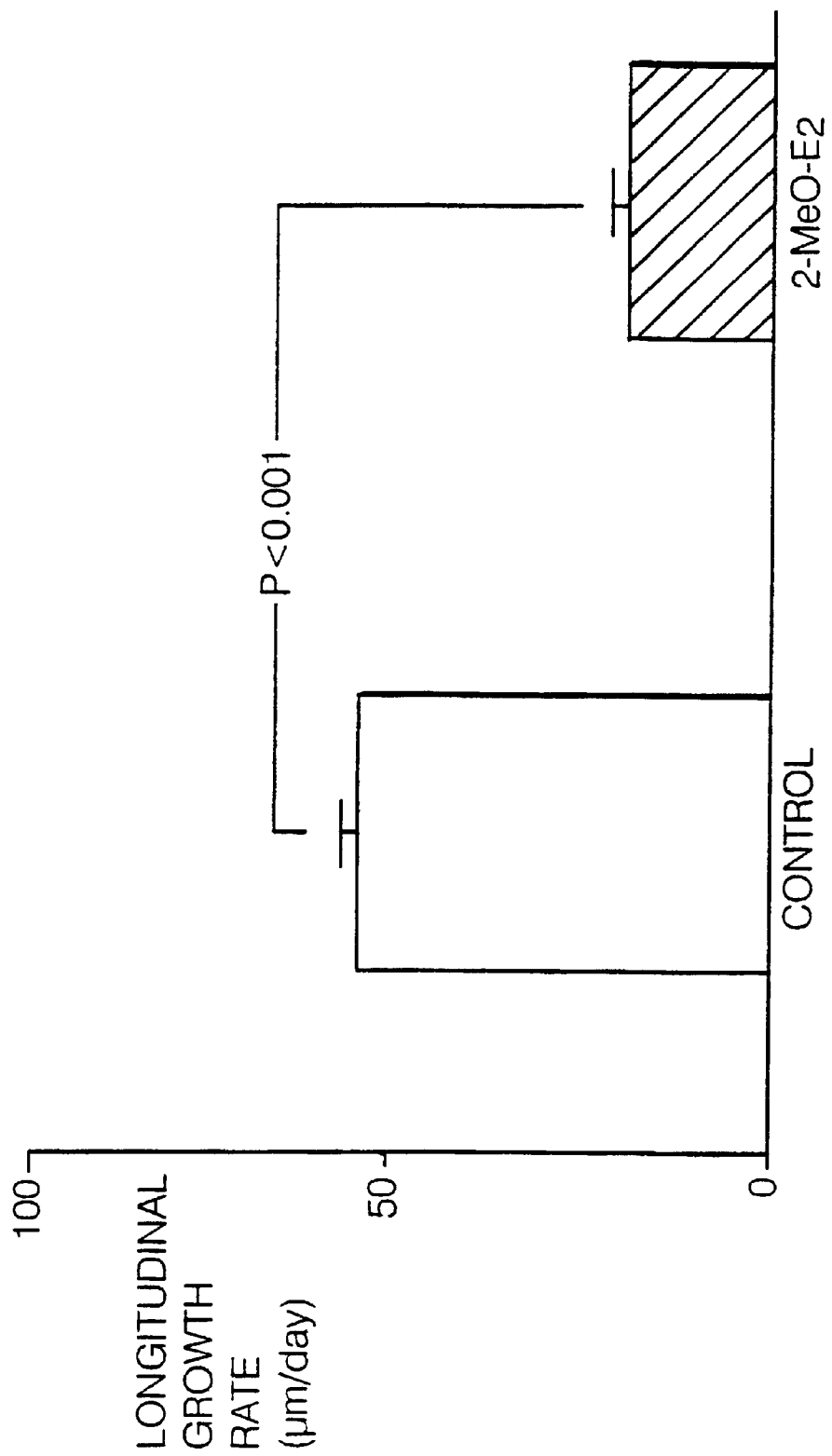
FIG. 2 is a graph depicting that 2ME treatment decreased longitudinal growth rate at the proximal end of the tibia. Values are reported as mean±SE, n=7–9.

Measurements of cortical bone histomorphometry did not respond to treatment, as documented in Table 1. Neither age nor 2ME had any effect on cross-sectional bone area, medullary area, and calculated cortical bone area. Additionally, 2ME treatment had no effect on the fluorochrome based cortical bone indices. Similarly, 2ME had no effect on cancellous bone histomorphometry as seen in Table 2. Neither age nor treatment altered cancellous bone volume expressed using tissue volume as the referent, trabecular number, trabecular thickness, and trabecular separation. Treatment had no effect on either the static or fluorochrome based cortical and cancellous bone measurements. 2ME treatment did not alter uterine wet weight, but did result in highly significant decreases in serum cholesterol (FIG. 1) and longitudinal bone growth (FIG. 2).

TABLE 1

Lack of an Effect of 2ME on Cortical Bone Histomorphmetry

| Measurement | Baseline | Control | 2ME2 | P Value Baseline vs Control or 2ME | P Value 2ME vs Control |
|---|---|---|---|---|---|
| Cross-sectional area (mm$^2$) | 2.93 ± 0.03 | 3.04 ± 0.03 | 2.98 ± 0.04 | NS | NS |
| Medullary Area (mm$^2$) | 0.63 ± 0.02 | 0.66 ± 0.03 | 0.70 ± 0.02 | NS | NS |
| Cortical Area | 2.29 ± 0.02 | 2.39 ± 0.03 | 2.28 ± 0.03 | NS | NS |
| Mineral Apposition Rate ($\mu$m/day) | — | 1.46 ± 0.09 | 1.34 ± 0.06 | — | NS |
| Bone Formation Rate (mm$^2$ × 10$^{-3}$/day) | — | 6.24 ± 0.53 | 5.32 ± 0.47 | — | NS |

Values are mean ± SE; N = 7–9.

TABLE 2

Lack of an Effect of 2ME on Cancellous Bone Histomorphometry

| Measurement | Baseline | Control | 2ME2 | P Value Baseline vs Control or 2ME | P Value 2ME vs Control |
|---|---|---|---|---|---|
| BV/TV (%) | 15.8 ± 2.4 | 18.0 ± 1.5 | 17.7 ± 1.9 | NS | NS |
| Tb.N (mm$^1$) | 2.82 ± 0.28 | 2.98 ± 0.18 | 3.03 ± 0.25 | NS | NS |
| Tb.Th ($\mu$m) | 55 ± 3 | 60 ± 2 | 57 ± 2 | NS | NS |
| Tb.Sp ($\mu$m) | 317 ± 38 | 281 ± 22 | 297 ± 46 | NS | NS |
| Mineral Apposition Rate ($\mu$m/day) | — | 168 ± 0.04 | 172 ± 0.05 | — | NS |
| BFR/BS (%/day) | — | 0.45 ± 0.02 | 0.35 ± 0.03 | — | NS |

Values are mean ± SE; N = 7–9. Cancellous bone volume (BV), tissue volume (TV), trabecular number (Tb.N), trabecular thickness (Tb.Th), trabecular separation (Tb.Sp.), bone formation rate (BFR), and bone surface (BS).

Effects of 2ME on growth plate histomorphometry are documented in Table 3. Treatment resulted in a highly significant decrease in height of the proliferative and hypertrophic zones of the growth plate, as well as total growth plate height. Treatment of rats with 2ME dramatically reduced longitudinal bone growth rate from 55±2 to 20±2 $\mu$m/day (p<0.001) and growth plate thickness from 153±14 to 70±6 $\mu$m (p<0.001). The latter decrease was due to significant reductions in the height of both the proliferative (p<0.001) and the hypertrophic (p<0.001) zones.

Thus, these studies demonstrate that 2ME has the ability to discriminate between one bone compartment and another, as well as between reproductive and non-reproductive estrogen-target tissues. Thus, 2ME is a naturally produced estrogen metabolite that demonstrates tissue selectivity.

Long bones increase in length by endochondral ossification, a process that involves rapid proliferation and hypertrophy of growth plate chondrocytes as well as angiogenesis associated with vascular invasion of the calcified cartilage. These bones increase in cross-sectional area by secondary intramembranous ossification at the periosteal surface. Radial bone growth contrasts with endochondral ossification in that the rate cell proliferation of periosteal cells is low compared to growth plate chondrocytes.

TABLE 3

2ME Treatment Alters Growth Plate Histomorphometry

| Measurement (thickness in $\mu$m) | Baseline | Control | 2ME | P Value Baseline vs. Control | P Value 2ME vs Baseline or Control |
|---|---|---|---|---|---|
| Growth plate | 136 ± 6 | 153 ± 14 | 70 ± 6 | NS | <0.001 |
| Hypertrophic zone | 39 ± 4 | 46 ± 6 | 6 ± 2 | NS | <0.001 |
| Proliferative zone | 45 ± 2 | 42 ± 5 | 11 ± 3 | NS | <0.001 |

Values are mean ± SE; N = 4–8.

Example 3

Cytotoxicity of 2ME to Osteosarcoma Cells

MG63 and TE85 human osteosarcoma cells, and ROS 17/2.8 rat osteosarcoma cells were grown in DMEM/F12 phenol-red free medium containing 10% charcoal-stripped fetal bovine serum (FBS) and supplemented with 100 units/ml penicillin, 100 µg/ml streptomycin. Cell were incubated at 37° C. under 5% $CO_2$ in air. Cells were plated at $5 \times 10^4$ cells per well into 24 well plates containing 1 ml of medium per well. After allowing the cells to attach overnight, media in the wells were replaced with fresh 1 ml medium. Human fetal osteoblasts (hFOB) cells and hFOB cells overexpressing estrogen receptor-alpha (hFOB-ERα) and estrogen receptor-beta (hFOB-ERβ) were grown in DMEM/F12 medium containing FBS, penicillin, streptomycin and Geneticin (300 µg/mL). The laboratory of Dr. B. L. Riggs at Mayo Clinic provided primary human osteoblast (HOB) cells. HOB cells were basically established from cancellous bone obtained as waste from orthopedic procedures and cultured as explants to generate the osteoblast-like monolayers as described by Borke et al., *J. Clin. Endocrinol. Metab.*, 1988, 67:1299–1304. Human FOB cells and hFOB cells stably transfected with estrogen receptors (ERs) were maintained at 34° C., while all other cells were incubated at 37° C. under 5% $CO_2$ in air.

Estrogen metabolites were diluted 1000 fold to give the final required concentrations in each well, and maintained for 72 hrs. The metabolites 2ME, 2OHE, and $E_2$ were purchased from Sigma Chemical Company (St. Louis, Mo.). Stock solutions for each metabolite were made in 95% ethanol. Cell growth was measured by taking the viable cell count. At the end of metabolite treatment, cells were harvested, stained with trypan blue, and counted under a light microscope.

Figure 3:
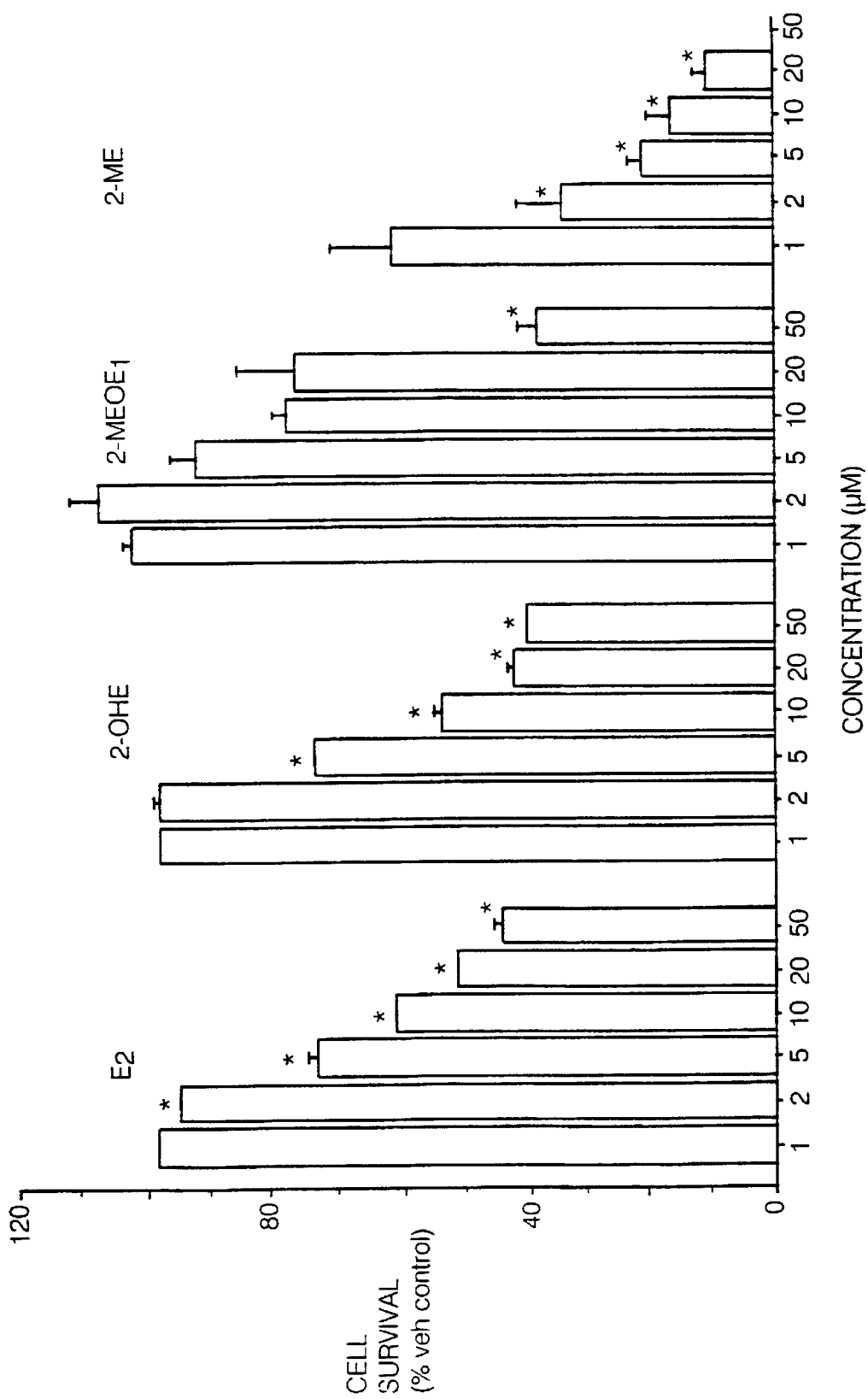
FIG. 3 is a graph depicting cell survival (% of control) of estradiol ($E_2$), 2-hydroxyestradiol (2OHE), 2-methoxyestrone ($2MEOE_1$), and 2ME treated MG63 cells (6 independent treatments). Values are the mean±SE; N=3–18 replicate cultures. *P≦0.05 (compared to ethanol vehicle control (Veh), by one way ANOVA and Fisher's PLSD analysis). The absence of error bar denotes a line thickness greater than error.

As indicated in FIG. 3, 2 µM of 2ME reduced MG63 cell survival by approximately 80% after 72 hours of treatment. At 20 and 50 µM, about 95% and 100% cell death was observed with 2ME. In comparison, 2 µM of 17-beta estradiol and 2-hydroxy estradiol had little impact on cell survival. At 20 and 50 µM, about 40% and 50% cell survival was observed with either 2OHE or $E_2$, respectively. Similar results were observed when 2-methoxyestrone (1–50 µM) was used (FIG. 3).

Figure 4:
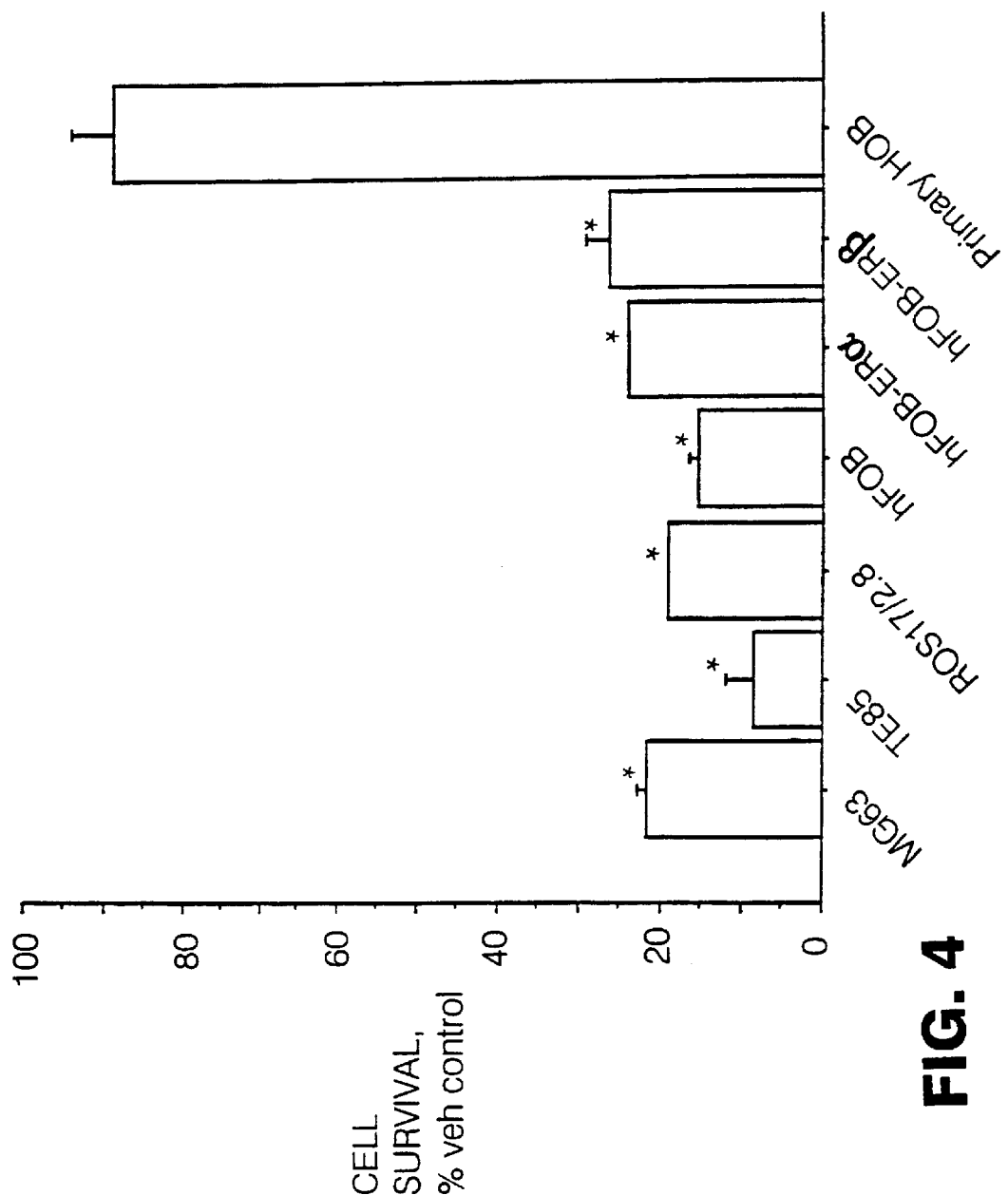
FIG. 4 is a graph depicting the effect of 2ME on osteoblasts and osteoblast-like cells. Values are the mean±SE; N=3 replicate cultures. *P≦0.05 (compared to ethanol vehicle control (Veh), by one way ANOVA and Fisher's PLSD analysis). The absence of error bar denotes a line thickness greater than error.

The effect of 2 µM 2ME on the proliferation of several osteoblastic cell lines (MG63, TE85, ROS17/2.8, hFOB, hFOB-Erα, and hFOB-ERβ) and primary osteoblasts (primary HOB) were studied at the end of 72 h of treatment (FIG. 4). The cell survival rate for human osteosarcoma cells MG63 and TE85 were reduced to 21% and 9%, respectively. Rat osteosarcoma ROS17/2.8 cell numbers were reduced to 19%. The cell numbers for immortalized human FOB cells, FOB cells expressing ER-α, and FOB cells expressing ER-β were reduced to 15%, 24% and 24%, respectively. At the end of 72 h, the survival of normal HOB cells derived from adult patients was 89%.

Figure 5:
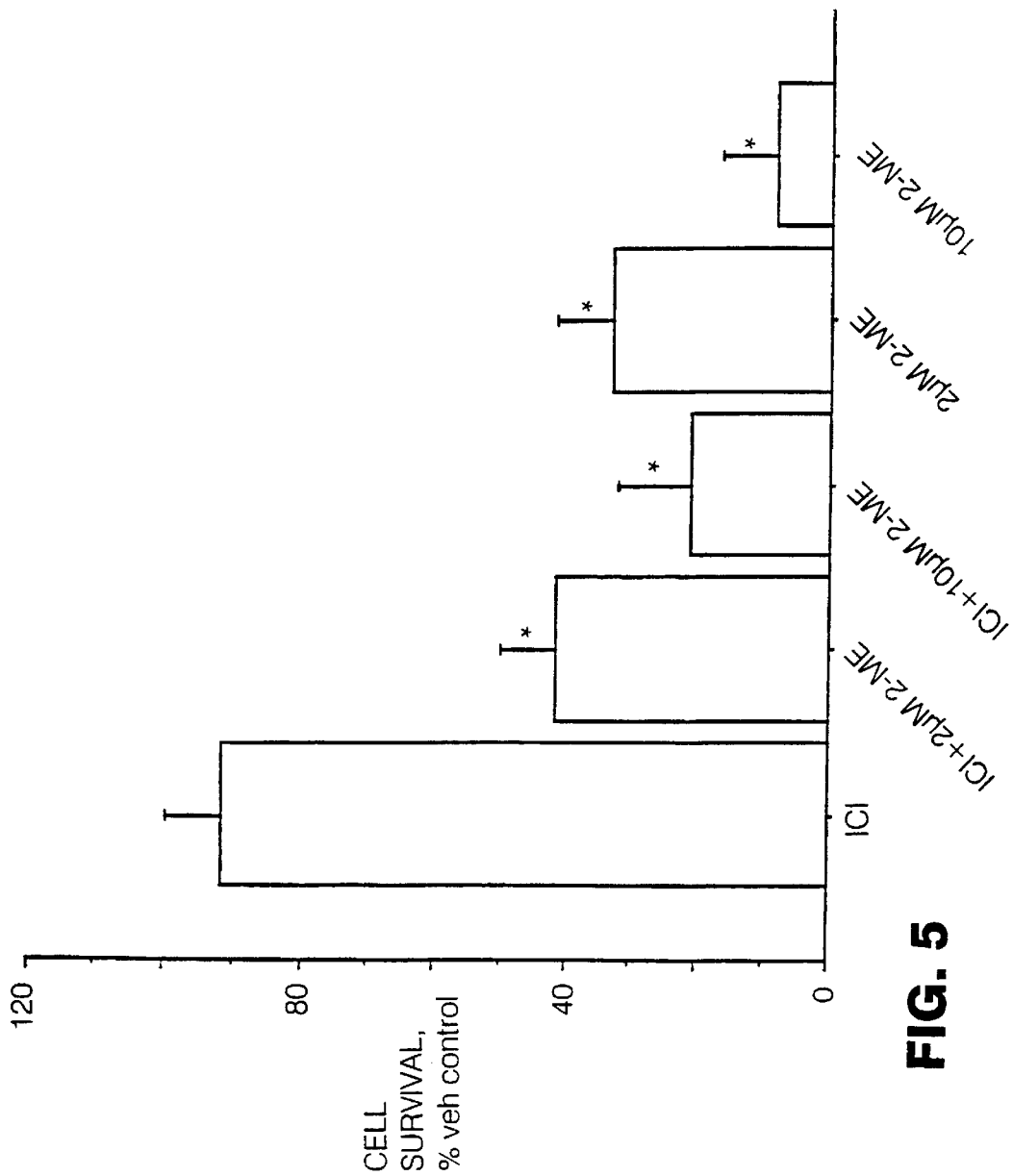
FIG. 5 is a graph depicting effect of antiestrogen ICI 182,780 (ICI) on 2ME mediated cell death. Values are the mean±SE; N=3 replicate cultures. *P≦0.05 (compared to ethanol vehicle control (Veh), by one way ANOVA and Fisher's PLSD analysis).

Estrogen receptor function does not appear to be required for cytotoxicity, as the antiestrogen compound ICI 182,780 does not block the killing of osteosarcoma cells. MG63 cells were treated with 0, 2, and 10 µM concentrations of 2ME in the presence or absence of 100 nM ICI for 72 hours. The cells were harvested and the viable cell counts were taken after staining with trypan blue. As indicated in FIG. 5, treatment with ICI had little impact on cell survival, whereas cell survival of ICI+2ME (2 µM or 10 µM) treated cells was reduced to less than about 40% of control.

Example 4

Effect of 2ME on Bone Matrix Gene Expressions

Time course effects of 2ME on steady-state mRNA levels for bone matrix proteins were determined. MG63 cells in triplicate cultures were treated with 10 µM 2ME. Cells were harvested at the end of 0, 12, 24 and 72 h of treatment and used for RNA isolation. Total RNA isolated from cells was analyzed by northern blot hybridization. Ten µg of RNA sample were denatured by incubation at 52° C. in a solution of 1M glyoxal, 50% dimethyl sulfoxide, and 0.01 M $NaH_2PO_4$, and then separated in a 1% agarose gel. RNA separated in agarose gels was transferred to an Amersham Hybond nylon membrane overnight via capillary action in 20× standard saline citrate (SSC) (1×SSC=0.15 M NaCl and 0.015 M sodium citrate, pH 7.0), sodium citrate buffer. The amounts of RNA loaded and transferred were assessed by methylene blue staining of the membranes and hybridization with a [$^{32}$P]-labeled cDNA for 18S ribosomal RNA. Membranes were prehybridized for 2 h at 65° C. in buffer containing 50% deionized formamide, 10% dextran sulfate, 5×SSC, 100 µg/ml of heat-denatured single-strand salmon sperm DNA, and 2× Denhardts solution. Hybridization was conducted for 80 min in a buffer containing the above ingredients in addition to a minimum of $10^6$ cpm per mL [$^{32}$P]-labeled cDNA probe. Labeled type I collagen and osteonectin cDNA were used for probing the blots. The cDNA probes were labeled by random sequence hexanucleotide primer extension using the Megaprime DNA labeling kit from Amersham (Arlington Heights, Ill.). The membranes were washed for 30 min at 45° C. in 2×SSC and for 15 to 60 min in 0.1×SSC at 45° C. The resulting radioactive mRNA bands on the blots were quantitated by Phosphorimager (Molecular Dynamics, Sunnyvale, Calif.).

Figure 6:
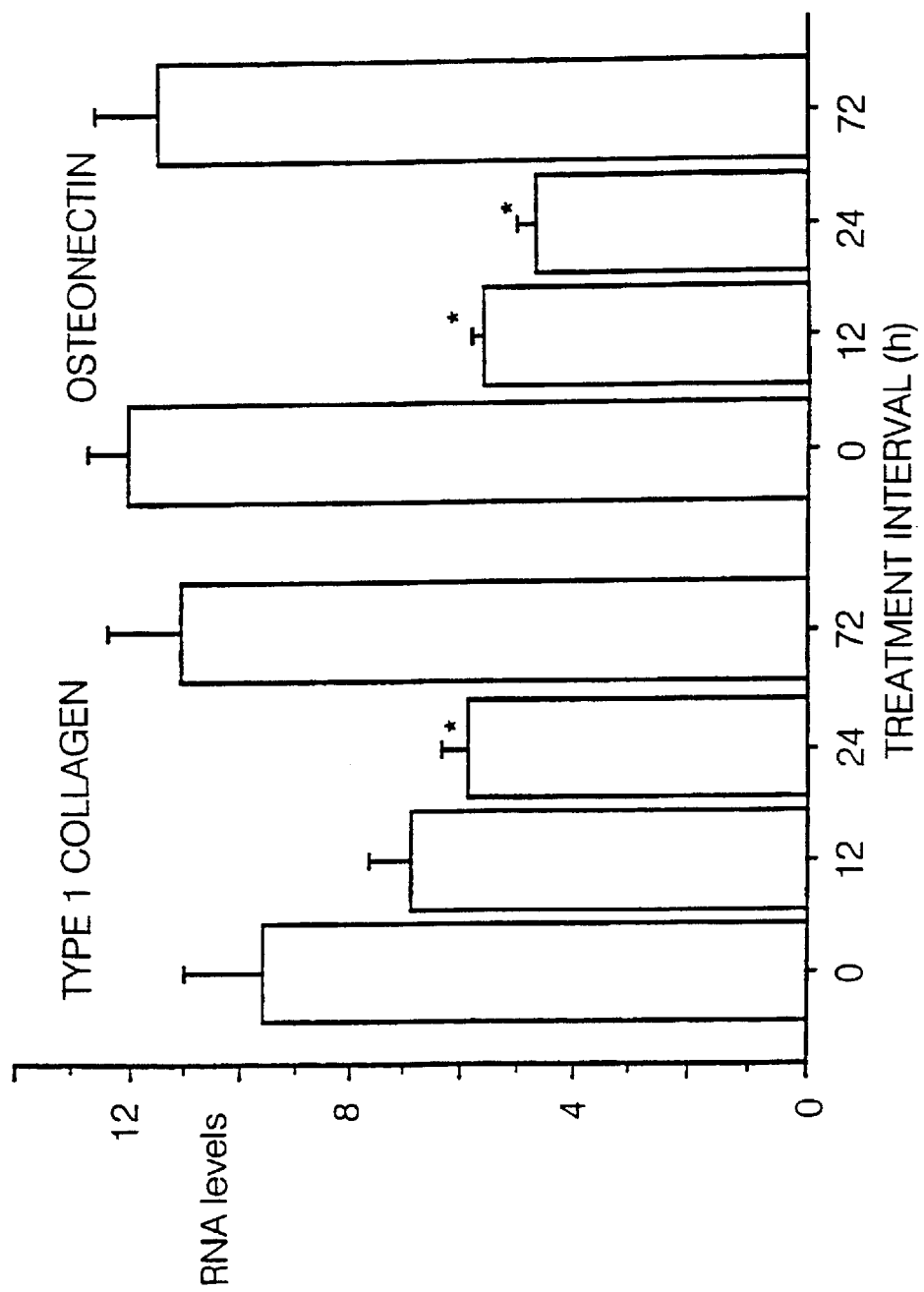
FIG. 6 is a graph indicating 2ME treatment leads to a decrease in bone matrix gene expression. Values are the mean±SE; N=3 replicate cultures. *P≦0.05 (compared to ethanol vehicle control (Veh), by one way ANOVA and Fisher's PLSD analysis).

2ME treatment led to transient decreases in type 1 collagen mRNA levels by 26% and 37% and osteonectin levels by 50% and 38% after 12 and 24 h, respectively (FIG. 6). The mRNA levels for the bone matrix proteins returned to normal levels by 72 h. Without being bound by a particular mechanism, 2ME may be metabolized in the cells. Osteonectin and type 1 collagen are markers for mature osteoblasts. 2ME resulted in dramatic, but transient reductions in steady-state MRNA levels for these two bone matrix proteins, indicating that 2ME inhibits osteoblast differentiation. Alternatively, 2-ME may selectively kill the more highly differentiated cells.

Example 5

Induction of Apoptotic Genes by 2ME Treatment

The effect of 2ME on in situ apoptosis was examined at the single cell level, based on labeling of DNA strand breaks using the TUNEL (terminal deoxynucleotidyl transferase-mediated dUTP nick end labeling) assay per manufacturer's protocol (Boehringer Mannheim, Indianapolis, Ind.). In this method, the ends of broken DNA strands were labeled with fluorescein-dUTP, and apoptotic cells in adherent cultures were detected by fluorescence microscopy. In brief, TUNEL assay was performed on coverslips of adherent cells contained in individual wells of a 24-well culture dish. Cells were washed once with phosphate buffered saline (PBS) and allowed to air dry before being fixed in 4% phosphate-buffered paraformaldehyde pH 7.4 (Sigma, St. Louis, Mo.) for 1 h at room temperature. Following a PBS rinse, endogenous peroxidase was blocked by incubating cells for 1 h at room temperature with 0.3% hydrogen peroxide in methanol (Sigmna). The latter was performed for the option of converting fluorescein-labeled cells to peroxidase-labeled cells and DAB chromogenic detection. Subsequent to a PBS rinse, cells were permeabilized on ice with incubation in 0.1% Triton X-100 in 0.1% sodium citrate for 2 min. Coverslips were rinsed twice in PBS before the addition of TUNEL reaction mixture (100 μl). One well containing untreated cells was treated with DNase I (Promega, Madison, Wis.) 2 μg/ml for 10 min at room temperature to serve as a positive control for the TUNEL reaction. Coverslips were incubated in TUNEL reaction mixture for 1 h at 37° C. Coverslips were rinsed 3 times with PBS before visualization by fluorescence microscopy. Negative controls consisted of three different treatments: 1) 2ME treated cells incubated 1 h at 37° C. in the absence of transferase enzyme in the TUNEL mixture, 2) cells treated with vehicle only, and 3) untreated adherent cells. Positive staining of MG63 osteosarcoma cells was observed after exposure to 10 μM of 2ME for 48 h. In contrast, cells exposed to vehicle for 48 h had no staining. In an untreated control where DNA breaks were introduced by DNase I treatment, there was positive staining. An untreated MG63 control and cells exposed to 2ME but incubated in the absence of transferase enzyme in the TUNEL mixture did not show any staining.

Figure 7:
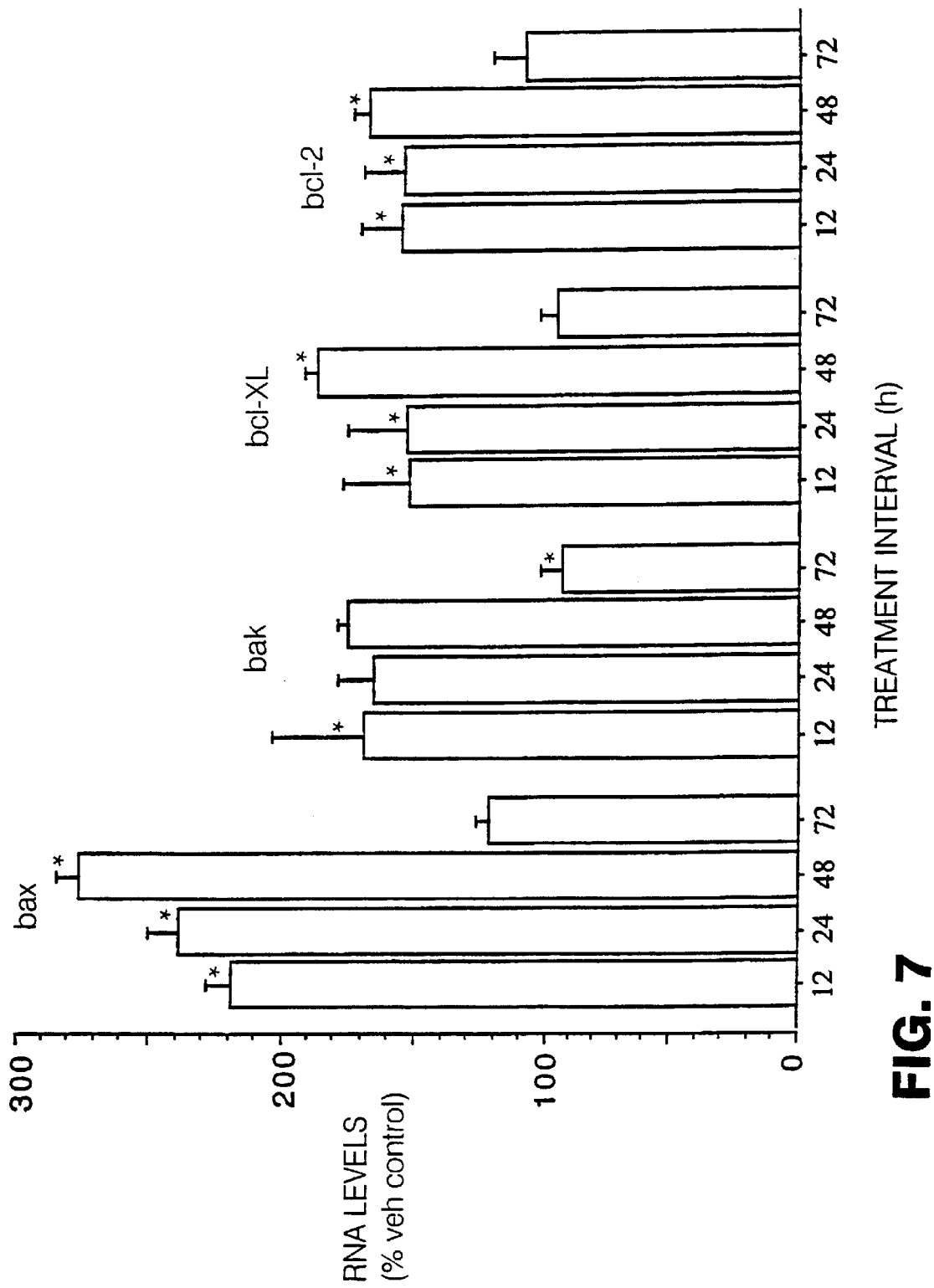
FIG. 7 is a graph depicting apoptotic gene mRNA levels at 12, 24, 48, and 72 hours (H12, H24, H48, H72, respectively) after 10 μM 2ME or ethanol vehicle control (VEH) treatment. Values are the mean±SE; N=3 replicate cultures. *P≦0.05 (compared to Veh, by one way ANOVA and Fisher's PLSD analysis). The absence of error bar denotes a line thickness greater than error.

The changes in expression of the genes that are known to antagonize or promote apoptosis were analyzed by this method. MG63 cells in triplicate cultures were treated with 10 μM 2ME. Cells were harvested at the end of 12, 24, 48 and 72 h of treatment and used for RNA isolation. Total RNA isolated from cells was analyzed by RNase protection assay using apoptosis template set for multiprobes (Pharmingen; San Diego, Calif.). Quantitation of protected RNA fragments was performed by Phosphor Imager analyses and normalized to L32 or GAP levels. The mRNA for the proapoptotic gene bak and bax were increased by 2ME treatment in MG63 cells (FIG. 7). The increase was significant within 12 h of treatment and reached a maximum (2 fold for bak; 2.5 fold for bax) at 48 h, at which time cell death by apoptosis was detected by in situ TUNEL assay. The mRNA levels for bak and bax returned to basal level at 72 h (FIG. 7). The mRNA levels of anti-apoptotic gene bcl-2 and bcl-XL showed a similar timecourse increase (FIG. 7).

The observed positive TUNEL assay indicates that 2ME induced cell death in osteosarcoma cells by apoptosis. This conclusion is supported by results demonstrating that 2ME treatment increased steady-state mRNA levels for genes related to apoptosis. The upregulation of several markers of apoptotic events in 2ME treated cells reflect the activation of signaling cascades implicated in programmed cell death. Simultaneous induction of proapoptotic and antiapoptotic genes has been demonstrated during the onset of apoptosis in osteoblasts. Lynch et al., *J. Cell Biochem.*, 1998, 68:31–49. The bax protein homodimers have been proposed to accelerate cell death, and this can be blocked by bax heterodimerization with bcl-2 and bcl-XL. Oltvai et al., *Cell*, 1993, 74:609–619. Since the phosphorylated form of bcl-2 protein loses its ability to induce apoptosis and the bax/bcl-2 expression ratio, as well as the subcellular localization of bax, bcl-2 and bcl-XL determine the pathway of apoptosis, further analysis at protein levels are required to address the actual role of these proteins in 2ME induced apoptosis.

Introduction of programmed cell death in osteosarcoma cells may involve interferon induced signal transduction pathways, as interferon-regulated proteins have been shown to induce programmed cell death, Example 6

Effect of 2ME Treatment on Cytokines and Growth Factors

Figure 8:
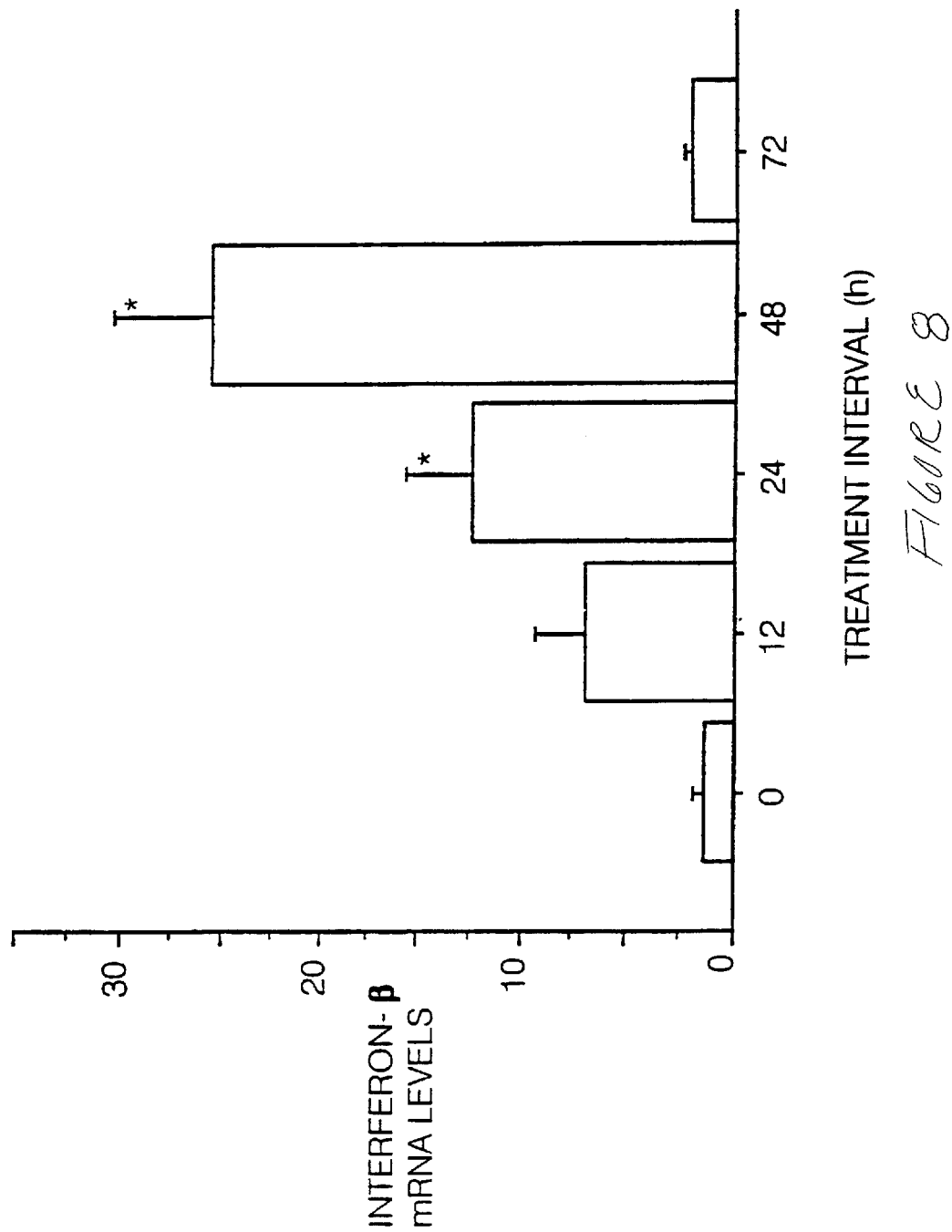
FIG. 8 is a graph depicting induction of interferon-β mRNA levels by 2ME treatment, as quantitated by PhosphorImager. Values are the mean±SE; N=3 replicate cultures. *P≦0.05 (compared to 0 time point by one way ANOVA and Fisher's PLSD analysis).

Changes in steady state mRNA levels for cytokines implicated in the regulation of bone formation and resorption were measured using RNase Protection assays. For RNA isolation and RNase protection assays, MG63 cells were plated at $10^6$ cells per T75 culture flask a day prior to metabolite treatment. The next day, the medium was removed and replaced with fresh medium containing 10 μM concentrations of 2ME and incubated for 12, 24, 48, and 72 hours. Cells were harvested and cell pellets were used for RNA isolation. Total cellular RNA was extracted and isolated using a modified organic solvent method and the RNA yields were determined spectrohotometrically at 260 nm. Total cellular RNA was analyzed by RNase protection assays using antisense RNA probes for transforming growth factor-beta (TGF-β), tumor necrosis factor (TNF) α and β, interleukin (IL) 1α, 1β, 1Ra, 6, 10, 12 (p35 and p40), interferon (IFN) β and γ, and lymphotoxin (LT) β. Quantitation of protected RNA fragments was performed by PhosphorImager analyses and normalized to ribosomal structural protein L32 or glyceraldehyde 3-phosphate dehydrogenase levels. Results are presented in FIG. 8 and Table 4, and are representative of 3 independent treatments.

While many cytokine genes were not detected in either control or 2-ME treated cultures (Table 4), there were 2-ME induced increases in the mRNA levels of Interferon-β(FIG. 8), TGF-β1, TGF-β2 and TGF-β3 (Table 4). The interferon-β mRNA level was increased by 500% within 12 h of 2-ME treatment and reached a maximum of 2100% by 48 h. TGF-β1, TGF-β2 and TGF-β3 mRNA levels were increased by 177%, 289% and 178%, respectively, and thereby showed a modest response to 2ME treatment.

TABLE 4

| Cytokine mRNAs analyzed in 2ME treated MG63 cells | |
|---|---|
| IL-12 p35 | Not detected |
| IL-12 p40 | Not detected |
| IL-10 | Not detected |
| IL-6 | Not detected |
| IL-1α | Not detected |
| IL-1β | Not detected |
| IL-1 Ra | Not detected |
| IFN-β | Increased |
| IFN-γ | Not detected |
| LT-β | Not detected |
| TNF-α | Not detected |
| TNF-β | Not detected |
| TGF-β1 | Increased |
| TGF-β2 | Increased |
| TGF-β3 | Increased |

Interferon-β and TGF-β mediated induction of apoptotic pathways are well established. However, this is the first study implicating these pathways in 2ME induced programmed cell death. Earlier studies have implicated a p53 gene mediated pathway in 2ME induction of programmed cell death. Mukhopadhyay et al., *Oncogene*, 1997, 14:379–384. Thus, 2ME may induce multiple pathways that lead to programmed cell death.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating bone cancer in a patient, said method comprising administering an amount of 2-methoxyestradiol to said patient, wherein said amount of 2-methoxyestradiol is cytotoxic to bone cancer cells.

2. The method of claim 1, wherein said bone cancer is an osteosarcoma.

3. The method of claim 1, wherein said bone cancer is a chondrosarcoma.

4. A method for killing bone cancer cells, said method comprising contacting said bone cancer cells with an amount of 2-methoxyestradiol, wherein said amount of 2-methoxyestradiol is cytotoxic to said bone cancer cells.

5. The method of claim 4, wherein said bone cancer cells are human cells.

6. The method of claim 4, wherein said bone cancer cells are osteosarcoma cells.

7. The method of claim 4, wherein said bone cancer cells are chondrosarcoma cells.

8. The method of claim 4, wherein said cells are contacted in vitro.

9. The method of claim 4, wherein said cells are contacted in vivo.

* * * * *

UNITED STATES PATENT AND TRADEMARK OFFICE
CERTIFICATE OF CORRECTION

PATENT NO. : 6,730,665 B1  Page 1 of 1
DATED : May 4, 2004
INVENTOR(S) : Avudaiappan Maran and Russell T. Turner It is certified that error appears in the above-identified patent and that said Letters Patent is hereby corrected as shown below:

Column 1,
Line 3, after title and before Cross-Reference to Related Applications, please insert the following paragraph:

-- STATEMENT AS TO FEDERALLY SPONSORED RESEARCH
Funding for the work described herein was provided by the federal government (NIH Grant No. AR41418), which may have certain rights in the invention. --

Signed and Sealed this

Thirteenth Day of July, 2004

JON W. DUDAS
*Acting Director of the United States Patent and Trademark Office*